(12) United States Patent
Peng et al.

(10) Patent No.: US 12,159,402 B2
(45) Date of Patent: Dec. 3, 2024

(54) BRAIN IMAGING NEUROLOGICAL ABNORMALITY PREDICTION SYSTEM AND OPERATION METHOD THEREOF

(71) Applicants: Taipei Medical University (TMU), Taipei (TW); TAIPEI VETERANS GENERAL HOSPITAL, Taipei (TW)

(72) Inventors: Syu-Jyun Peng, Hsinchu County (TW); Chien-Chen Chou, Taipei (TW); Yen-Cheng Shih, Taipei (TW); Hsu-Huai Chiu, Taoyuan (TW)

(73) Assignees: Taipei Medical University (TMU), Taipei (TW); TAIPEI VETERANS GENERAL HOSPITAL, Taipei (TW)

( * ) Notice: Subject to any disclaimer, the term of this patent is extended or adjusted under 35 U.S.C. 154(b) by 358 days.

(21) Appl. No.: 17/662,659

(22) Filed: May 10, 2022

(65) Prior Publication Data

US 2022/0398722 A1    Dec. 15, 2022

(30) Foreign Application Priority Data

Jun. 15, 2021    (TW) .................................. 110121795

(51) Int. Cl.
| | |
|---|---|
| *G06T 7/00* | (2017.01) |
| *A61B 5/00* | (2006.01) |
| *A61B 5/1455* | (2006.01) |
| *G16H 50/20* | (2018.01) |
| *G16H 50/30* | (2018.01) |
| *G16H 50/70* | (2018.01) |

(52) U.S. Cl.
CPC ........ *G06T 7/0012* (2013.01); *A61B 5/14553* (2013.01); *A61B 5/4094* (2013.01); *G16H 50/20* (2018.01); *G16H 50/30* (2018.01); *G16H 50/70* (2018.01); *G06T 2207/30016* (2013.01)

(58) Field of Classification Search
None
See application file for complete search history.

(56) References Cited

U.S. PATENT DOCUMENTS

| | | | |
|---|---|---|---|
| 2019/0122348 A1* | 4/2019 | Jensen | G16H 50/50 |
| 2020/0104995 A1* | 4/2020 | Akahori | G06T 7/11 |

FOREIGN PATENT DOCUMENTS

| | | |
|---|---|---|
| CN | 103181762 B | 5/2015 |
| TW | 680744 B | 1/2020 |

* cited by examiner

*Primary Examiner* — Leon Flores
(74) *Attorney, Agent, or Firm* — CKC & Partners Co., LLC

(57) ABSTRACT

The present disclosure provides an operating method of a brain imaging neurological abnormality prediction system, which includes steps as follows. The T1-weighted image and the diffusion-weighted image of the patient are acquired; the image process is performed on the T1-weighted image and the diffusion-weighted image to obtain a smoothed brain standard space infarction image; the smoothed brain standard space infarction image is multiplied by and a weighted image for a post-processing to obtain a post-weight image; the post-weight image is inputted to the deep learning cross validation classification model of transfer learning to predict whether the neurological abnormality occurs within a predetermined period after the patient's brain disease.

15 Claims, 2 Drawing Sheets

BRAIN IMAGING NEUROLOGICAL ABNORMALITY PREDICTION SYSTEM AND OPERATION METHOD THEREOF

RELATED APPLICATIONS

This application claims priority to Taiwan Patent Application No. 110121795, filed Jun. 15, 2021, the entirety of which is herein incorporated by reference.

BACKGROUND

Field of Invention

The present invention relates to systems and methods, and more particularly, brain imaging neurological abnormality prediction systems and operation methods thereof.

Description of Related Art

Stroke may cause death as well as disability, which often increases a great burden on the family and even the whole country. The post-stroke seizure is an important complication after stroke, accounting for about 2-4% of stroke patients. Its occurrence not only increases the rate of mortality and morbidity, but also decreases the quality of life in the patients with stroke.

Therefore, it is very important to know who have high probability of suffering from post-stroke seizure. This provides an opportunity to reach the goal of early treatment and prevention of post-stroke seizure.

SUMMARY

In one or more various aspects, the present disclosure is directed to brain imaging neurological abnormality prediction systems and operation methods thereof.

An embodiment of the present disclosure is related to a brain imaging neurological abnormality prediction system. The brain imaging neurological abnormality prediction system includes a memory circuit and a processor. The memory circuit is configured to store at least one instruction. The processor coupled to the memory circuit, and the processor configured to access and execute the at least one instruction for: acquiring a T1-weighted image and a diffusion-weighted image (DWI) of a patient; performing an image process on the T1-weighted image and the DWI to obtain a smoothed brain standard space infarction image; multiplying the smoothed brain standard space infarction image by a weighted image for a post-processing, so as to obtain a post-weight image; inputting the post-weight image to a deep learning cross validation classification model of a transfer learning to predict whether a neurological abnormality occurs within a predetermined period after a brain disease of the patient.

In one embodiment of the present disclosure, the processor accesses and executes the at least one instruction for: linearly co-registering the T1-weighted image to the DWI, so as to generate a co-registered T1-weighted image; spatially normalizing the co-registered T1-weighted image to a T1 template to obtain spatially normalization parameters; marking a cerebral infarction area in the DWI to generate a cerebral infarction mask image; normalizing the cerebral infarction mask image in a standard brain space through the spatially normalization parameters to obtain a normalized cerebral infarction mask image of the standard brain space; smoothing the normalized cerebral infarction mask image of the standard brain space to obtain the smoothed brain standard space infarction image.

In one embodiment of the present disclosure, the processor accesses and executes the at least one instruction for: statistically compare brain images of a plurality of groups of historical patients with the neurological abnormality within the predetermined period after the brain disease to brain images of a plurality of groups of historical patients without the neurological abnormality within the predetermined period after the brain disease, so as to find out a hot area correlated to the neurological abnormality within the predetermined period after the brain disease, and serving the hot area as the weighted image.

In one embodiment of the present disclosure, the smoothed brain standard space infarction image and the weighted image both are three-dimensional images, the post-processing is a dimension reduction operation, and the processor accesses and executes the at least one instruction for: multiplying the smoothed brain standard space infarction image by a weighted image to obtain a three-dimensional product image; performing the dimension reduction operation on the three-dimensional product image to obtain the post-weight image.

In one embodiment of the present disclosure, the brain disease is a stroke, the predetermined period is one year, and the neurological abnormality is seizure.

Another embodiment of the present disclosure is related to an operation method of a brain imaging neurological abnormality prediction system. The operation method includes steps of: acquiring a T1-weighted image and a DWI of a patient; performing an image process on the T1-weighted image and the DWI to obtain a smoothed brain standard space infarction image; multiplying the smoothed brain standard space infarction image by a weighted image for a post-processing to obtain a post-weight image; inputting the post-weight image to a deep learning cross validation classification model of a transfer learning to predict whether a neurological abnormality occurs within a predetermined period after a brain disease of the patient.

In one embodiment of the present disclosure, the operation method further includes steps of: linearly co-registering the T1-weighted image to the DWI, so as to generate a co-registered T1-weighted image; spatially normalizing the co-registered T1-weighted image to a T1 template to obtain spatially normalization parameters; marking a cerebral infarction area in the DWI to generate a cerebral infarction mask image; normalizing the cerebral infarction mask image in a standard brain space through the spatially normalization parameters to obtain a normalized cerebral infarction mask image of the standard brain space; smoothing the normalized cerebral infarction mask image of the standard brain space to obtain the smoothed brain standard space infarction image.

In one embodiment of the present disclosure, the operation method further includes steps of: statistically compare brain images of a plurality of groups of historical patients with the neurological abnormality within the predetermined period after the brain disease to brain images of a plurality of groups of historical patients without the neurological abnormality within the predetermined period after the brain disease, so as to find out a hot area correlated to the neurological abnormality within the predetermined period after the brain disease, and serving the hot area as the weighted image.

In one embodiment of the present disclosure, the smoothed brain standard space infarction image and the weighted image both are three-dimensional images, the post-processing is a dimension reduction operation, and the step of multiplying the smoothed brain standard space infarction image by the weighted image for the post-processing to obtain the post-weight image includes: multiplying the smoothed brain standard space infarction image by a weighted image to obtain a three-dimensional product image; performing the dimension reduction operation on the three-dimensional product image to obtain the post-weight image.

In one embodiment of the present disclosure, the brain disease is a stroke, the predetermined period is one year, and the neurological abnormality is seizure.

Technical advantages are generally achieved, by embodiments of the present disclosure. With the brain imaging neurological abnormality prediction system and its operation method of the present disclosure, the deep learning cross validation classification model of the transfer learning (e.g., an artificial intelligence model for predicting the possibility of seizure after stroke) can be applied to the treatment decision as to the brain disease of the patient.

Many of the attendant features will be more readily appreciated, as the same becomes better understood by reference to the following detailed description considered in connection with the accompanying drawings.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
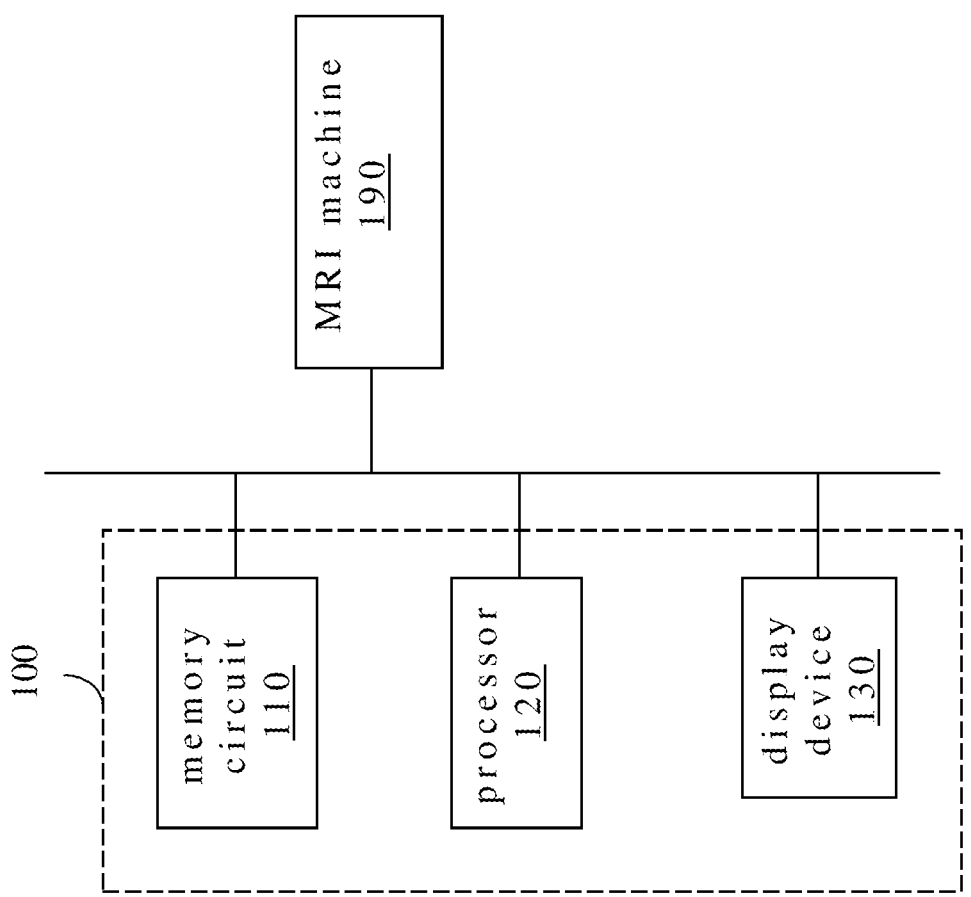
FIG. 1 is a block diagram of a brain imaging neurological abnormality prediction system according to one embodiment of the present disclosure.

Reference will now be made in detail to the present embodiments of the invention, examples of which are illustrated in the accompanying drawings. Wherever possible, the same reference numbers are used in the drawings and the description to refer to the same or like parts.

Referring to FIG. 1, in one aspect, the present disclosure is directed to a brain imaging neurological abnormality prediction system 100. The brain imaging neurological abnormality prediction system 100 may be easily integrated into a computer and may be applicable or readily adaptable to all technologies. Technical advantages are generally achieved by the brain imaging neurological abnormality prediction system 100 according to embodiments of the present disclosure. Herewith the brain imaging neurological abnormality prediction system 100 is described below with FIG. 1.

The subject disclosure provides the brain imaging neurological abnormality prediction system 100 in accordance with the subject technology. Various aspects of the present technology are described with reference to the drawings. In the following description, for purposes of explanation, numerous specific details are set forth in order to provide a thorough understanding of one or more aspects. It can be evident, however, that the present technology can be practiced without these specific details. In other instances, well-known structures and devices are shown in block diagram form to facilitate describing these aspects. The word "exemplary" is used herein to mean "serving as an example, instance, or illustration." Any embodiment described herein as "exemplary" is not necessarily to be construed as preferred or advantageous over other embodiments.

FIG. 1 is a block diagram of the brain imaging neurological abnormality prediction system 100 according to one embodiment of the present disclosure. As shown in FIG. 1, the brain imaging neurological abnormality prediction system 100 includes a memory circuit 110, a processor 120 and a display device 130. For example, the memory circuit 110 can be a hard drive, a flash memory or another storage device, the processor 120 can be a central processing unit, and a display device 130 can be a built-in the display screen or an external screen.

In structure, the brain imaging neurological abnormality prediction system 100 is coupled to a magnetic resonance imaging (MRI) machine 190, and the processor 120 is coupled to the memory circuit 110 and the display device 130. It should be noted that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. For example, the memory circuit 110 may be a built-in memory circuit that is directly connected to the processor 120, or the memory circuit 110 may be an external storage device that is indirectly connected to the processor 120 through the connection circuit.

In use, the memory circuit 110 store at least one instruction, the processor 120 is coupled to the memory circuit 110, and the processor 120 accesses and executes the at least one instruction for: acquiring a T1-weighted image and a diffusion-weighted image (DWI) of a patient. In practice, for example, the MRI machine 190 can obtain the T1-weighted image, the DWI, and an apparent diffusion coefficient (ADC) map of the patient.

Then, the processor 120 accesses and executes the at least one instruction for: performing an image process on the T1-weighted image, the DWI and the cerebral infarction mask of the patient to obtain a smoothed brain standard space infarction image.

Then, the processor 120 accesses and executes the at least one instruction for: multiplying the smoothed brain standard space infarction image by a weighted image for a post-processing, to obtain a post-weight image; inputting the post-weight image to a deep learning cross validation classification model of a transfer learning to predict whether a neurological abnormality occurs within a predetermined period after a brain disease of the patient. The display device 130 can display a result of above prediction.

As to the post-processing, in one embodiment of the present disclosure, the smoothed brain standard space infarction image and the weighted image both are three-dimensional images, the post-processing is a dimension reduction operation, and the processor 120 accesses and executes the at least one instruction for: multiplying the smoothed brain standard space infarction image by a weighted image to obtain a three-dimensional product image; performing the dimension reduction operation on the three-dimensional product image to obtain the post-weight image. Thus, the post-weighted image is a two-dimensional image.

As to the above-mentioned dimension reduction operation, in practice, for example, the three-dimensional product images are summed in the direction of a fixed axis (e.g., a Z axis) to obtain a two-dimensional post-weighted image.

As to the image process associated with the smoothed brain standard space infarction image, in one embodiment of the present disclosure, linearly co-registering the T1-weighted image to the DWI, so as to generate a co-registered T1-weighted image; spatially normalized the co-registered T1-weighted image to a T1 template to obtain spatially normalization parameters; marking a cerebral infarction area in the DWI to generate a cerebral infarction mask image; normalizing the cerebral infarction mask image in a standard brain space through the spatially normalization parameters to obtain a normalized cerebral infarction mask image of the standard brain space, so as to eliminate the influence of internal composition bias on subsequent results; smoothing the normalized cerebral infarction mask image of the standard brain space to obtain the smoothed brain standard space infarction image, thereby improving the signal-to-noise ratio. In practice, for example, the storage device 110 can pre-store the T1 template.

As to the way of marking a cerebral infarction area, in one embodiment of the present disclosure, the processor 120 executes conventional or developing software to automatically mark the cerebral infarction area in the DWI to generate the cerebral infarction mask image.

Alternatively, in another embodiment of the present disclosure, the processor 120 marks the cerebral infarction area in the DWI according to the cerebral infarction area manually inputted by a user (e.g., a doctor), to generate the cerebral infarction mask image. In practice, the doctor can manually input the cerebral infarction area by referring to the DWI and the ADC map.

As to the weighted image, in one embodiment of the present disclosure, the processor 120 accesses and executes the at least one instruction for: statistically compare brain images of a plurality of groups of historical patients with the neurological abnormality within the predetermined period after the brain disease to brain images of a plurality of groups of historical patients without the neurological abnormality within the predetermined period after the brain disease, so as to find out a hot area correlated to the neurological abnormality within the predetermined period after the brain disease, and serving the hot area as the weighted image.

In one embodiment of the present disclosure, the brain disease is a stroke, the predetermined period is one year, and the neurological abnormality is seizure. In practice, for example, by analyzing the stroke infarct areas of the MRI of the brains of the patients with acute ischemic stroke, the voxel-based analysis is used to statistically compare brain images of a plurality of groups (n=66) of historical patients with the seizure within the one year after the stroke to brain images of a plurality of groups (n=66) of historical patients without the seizure within one year after the brain stroke, in which, for example, above statistical comparison uses a two-sample t-test, two-tailed statistical p-value less than 0.05 and the smallest cluster size is 154, considered statistically significant. In this way, the "hot area" that is prone to post-stroke seizure due to the ischemic stroke can be found. This "hot area" image is further regarded as the weighted image for training the deep learning classification model, to enhance the weight interpretation of the epileptic infarct area after stroke for training.

By analyzing the stroke areas of the MRI of the brains of the patients with acute ischemic stroke, the "hot area" that is prone to post-stroke seizure due to the ischemic stroke can be found. The research did not discuss the scope of stroke about the risk factors of post-stroke seizure in the past, mainly focused on the calibration of large-scale brain regions (e.g., a frontal lobe, temporal lobe, parietal lobe, etc.), and there was no direct brain image analysis study. The present disclosure precisely represents the "hot area" of the post-stroke seizure.

Figure 2:
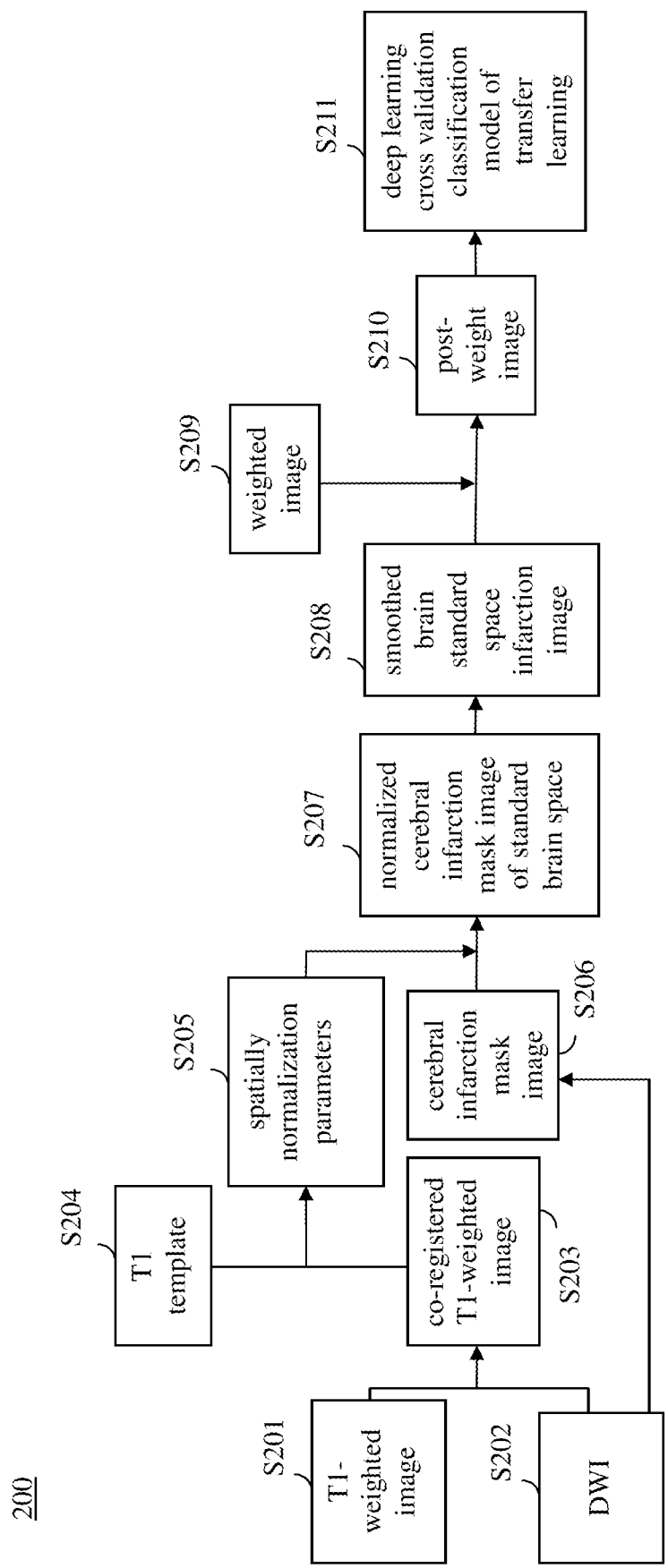
FIG. 2 is a flow chart of an operation method of the brain imaging neurological abnormality prediction system according to one embodiment of the present disclosure.

For a more complete understanding of an operation method of the brain imaging neurological abnormality prediction system 100, referring FIGS. 1-2, FIG. 2 is a flow chart of the operation method 200 of the brain imaging neurological abnormality prediction system 100 according to one embodiment of the present disclosure. As shown in FIG. 2, the operation method 200 includes operations S201-S211. However, as could be appreciated by persons having ordinary skill in the art, for the steps described in the present embodiment, the sequence in which these steps are performed, unless explicitly stated otherwise, can be altered depending on actual needs; in certain cases, all or some of these steps can be performed concurrently.

The operation method 200 may take the form of a computer program product on a computer-readable storage medium having computer-readable instructions embodied in the medium. Any suitable storage medium may be used including non-volatile memory such as read only memory (ROM), programmable read only memory (PROM), erasable programmable read only memory (EPROM), and electrically erasable programmable read only memory (EEPROM) devices; volatile memory such as SRAM, DRAM, and DDR-RAM; optical storage devices such as CD-ROMs and DVD-ROMs; and magnetic storage devices such as hard disk drives and floppy disk drives.

In operation S201, the T1-weighted image of a patient is acquired. In operation S202, the DWI of the patient is acquired. In operations S203-S208, the image process is performed on the T1-weighted image and the diffusion-weighted image to obtain a smoothed brain standard space infarction image. In operations S209-S210, the smoothed brain standard space infarction image is multiplied by and a weighted image for a post-processing to obtain a post-weight image. In operation S211, the post-weight image is inputted to the deep learning cross validation classification model of transfer learning to predict whether the neurological abnormality occurs within a predetermined period after a brain disease of the patient.

In one embodiment of the present disclosure, in operation S203, the T1-weighted image is linearly co-registered to the DWI, to generate a co-registered T1-weighted image. In operation S204, a T1 template is preloaded. In operation S205, the co-registered T1-weighted image is spatially normalized to the T1 template to obtain spatially normalization parameters. In operation S206, a cerebral infarction area is marked in the DWI to generate a cerebral infarction mask image. In operation S207, the cerebral infarction mask image is normalized in a standard brain space through the spatially normalization parameters to obtain a normalized cerebral infarction mask image of the standard brain space. In operation S208, the normalized cerebral infarction mask image of the standard brain space is smoothed to obtain the smoothed brain standard space infarction image.

In one embodiment of the present disclosure, in operation S209, brain images of a plurality of groups of historical patients with the neurological abnormality within the predetermined period after the brain disease are statistically compared to brain images of a plurality of groups of historical patients without the neurological abnormality within the predetermined period after the brain disease, so as to find out a hot area correlated to the neurological abnormality within the predetermined period after the brain disease, and serving the hot area as the weighted image. In one embodiment of the present disclosure, the brain disease is a stroke, the predetermined period is one year, and the neurological abnormality is seizure.

In one embodiment of the present disclosure, the smoothed brain standard space infarction image and the weighted image both are three-dimensional images, and the post-processing is a dimension reduction operation. In operation S210, the smoothed brain standard space infarction image is multiplied by a weighted image to obtain a three-dimensional product image; the dimension reduction operation is performed on the three-dimensional product image to obtain the post-weight image.

In view of the above, technical advantages are generally achieved, by embodiments of the present disclosure. With the brain imaging neurological abnormality prediction system 100 and its operation method 200 of the present disclosure, the deep learning cross validation classification model of the transfer learning (e.g., an artificial intelligence model for predicting the possibility of seizure after stroke) can be applied to the treatment decision as to the brain disease of the patient.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A brain imaging neurological abnormality prediction system, comprising:
    a memory circuit configured to store at least one instruction; and
    a processor coupled to the memory circuit, and the processor configured to access and execute the at least one instruction for:
        acquiring a T1-weighted image and a diffusion-weighted image (DWI) of a patient;
        performing an image process on the T1-weighted image and the DWI to obtain a smoothed brain standard space infarction image;
        multiplying the smoothed brain standard space infarction image by a weighted image for a post-processing, to obtain a post-weight image; and
        inputting the post-weight image to a deep learning cross validation classification model of a transfer learning to predict whether a neurological abnormality occurs within a predetermined period after a brain disease of the patient.

2. The brain imaging neurological abnormality prediction system of claim 1, wherein the processor accesses and executes the at least one instruction for:
    linearly co-registering the T1-weighted image to the DWI, to generate a co-registered T1-weighted image;
    spatially normalizing the co-registered T1-weighted image to a T1 template to obtain spatially normalization parameters;
    marking a cerebral infarction area in the DWI to generate a cerebral infarction mask image;
    normalizing the cerebral infarction mask image in a standard brain space through the spatially normalization parameters to obtain a normalized cerebral infarction mask image of the standard brain space; and
    smoothing the normalized cerebral infarction mask image of the standard brain space to obtain the smoothed brain standard space infarction image.

3. The brain imaging neurological abnormality prediction system of claim 1, wherein the processor accesses and executes the at least one instruction for:
    statistically compare brain images of a plurality of groups of historical patients with the neurological abnormality within the predetermined period after the brain disease to brain images of a plurality of groups of historical patients without the neurological abnormality within the predetermined period after the brain disease, so as to find out a hot area correlated to the neurological abnormality within the predetermined period after the brain disease, and serving the hot area as the weighted image.

4. The brain imaging neurological abnormality prediction system of claim 1, wherein the smoothed brain standard space infarction image and the weighted image both are three-dimensional images, the post-processing is a dimension reduction operation, and the processor accesses and executes the at least one instruction for:
    multiplying the smoothed brain standard space infarction image by a weighted image to obtain a three-dimensional product image; and
    performing the dimension reduction operation on the three-dimensional product image to obtain the post-weight image.

5. The brain imaging neurological abnormality prediction system of claim 1, wherein the brain disease is a stroke, the predetermined period is one year, and the neurological abnormality is seizure.

6. An operation method of a brain imaging neurological abnormality prediction system, and the operation method comprising steps of:
    acquiring a T1-weighted image and a diffusion-weighted image (DWI) of a patient;
    performing an image process on the T1-weighted image and the DWI to obtain a smoothed brain standard space infarction image;
    multiplying the smoothed brain standard space infarction image by a weighted image for a post-processing to obtain a post-weight image; and
    inputting the post-weight image to a deep learning cross validation classification model of a transfer learning to predict whether a neurological abnormality occurs within a predetermined period after a brain disease of the patient.

7. The operation method of claim 6, further comprising:
    linearly co-registering the T1-weighted image to the DWI, to generate a co-registered T1-weighted image;
    spatially normalizing the co-registered T1-weighted image to a T1 template to obtain spatially normalization parameters;
    marking a cerebral infarction area in the DWI to generate a cerebral infarction mask image;
    normalizing the cerebral infarction mask image in a standard brain space through the spatially normalization parameters to obtain a normalized cerebral infarction mask image of the standard brain space; and
    smoothing the normalized cerebral infarction mask image of the standard brain space to obtain the smoothed brain standard space infarction image.

8. The operation method of claim 6, further comprising:
    statistically compare brain images of a plurality of groups of historical patients with the neurological abnormality within the predetermined period after the brain disease to brain images of a plurality of groups of historical patients without the neurological abnormality within the predetermined period after the brain disease, so as to find out a hot area correlated to the neurological abnormality within the predetermined period after the brain disease, and serving the hot area as the weighted image.

9. The operation method of claim 6, wherein the smoothed brain standard space infarction image and the weighted image both are three-dimensional images, the post-processing is a dimension reduction operation, and the step of multiplying the smoothed brain standard space infarction image by the weighted image for the post-processing to obtain the post-weight image comprises:

multiplying the smoothed brain standard space infarction image by a weighted image to obtain a three-dimensional product image; and performing the dimension reduction operation on the three-dimensional product image to obtain the post-weight image.

10. The operation method of claim 6, wherein the brain disease is a stroke, the predetermined period is one year, and the neurological abnormality is seizure.

11. A non-transitory computer readable medium to store a plurality of instructions for commanding a computer to execute an operation method, and the operation method comprising steps of:

acquiring a T1-weighted image and a diffusion-weighted image (DWI) of a patient;

performing an image process on the T1-weighted image and the DWI to obtain a smoothed brain standard space infarction image;

multiplying the smoothed brain standard space infarction image by a weighted image for a post-processing to obtain a post-weight image; and inputting the post-weight image to a deep learning cross validation classification model of a transfer learning to predict whether a neurological abnormality occurs within a predetermined period after a brain disease of the patient.

12. The non-transitory computer readable medium of claim 11, wherein the operation method further comprises:

linearly co-registering the T1-weighted image to the DWI, to generate a co-registered T1-weighted image;

spatially normalizing the co-registered T1-weighted image to a T1 template to obtain spatially normalization parameters;

marking a cerebral infarction area in the DWI to generate a cerebral infarction mask image;

normalizing the cerebral infarction mask image in a standard brain space through the spatially normalization parameters to obtain a normalized cerebral infarction mask image of the standard brain space; and smoothing the normalized cerebral infarction mask image of the standard brain space to obtain the smoothed brain standard space infarction image.

13. The non-transitory computer readable medium of claim 12, wherein the operation method further comprises:

statistically compare brain images of a plurality of groups of historical patients with the neurological abnormality within the predetermined period after the brain disease to brain images of a plurality of groups of historical patients without the neurological abnormality within the predetermined period after the brain disease, so as to find out a hot area correlated to the neurological abnormality within the predetermined period after the brain disease, and serving the hot area as the weighted image.

14. The non-transitory computer readable medium of claim 13, wherein the smoothed brain standard space infarction image and the weighted image both are three-dimensional images, the post-processing is a dimension reduction operation, and the step of multiplying the smoothed brain standard space infarction image by the weighted image for the post-processing to obtain the post-weight image comprises:

multiplying the smoothed brain standard space infarction image by a weighted image to obtain a three-dimensional product image; and performing the dimension reduction operation on the three-dimensional product image to obtain the post-weight image.

15. The non-transitory computer readable medium of claim 11, the brain disease is a stroke, the predetermined period is one year, and the neurological abnormality is seizure.

* * * * *